(12) United States Patent
Matusch (10) Patent No.: US 8,372,035 B2
(45) Date of Patent: Feb. 12, 2013

(54) DISPOSABLE INJECTOR WITH MANUALLY ACTUATED PISTON

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 301 days.

(21) Appl. No.: 12/655,139

(22) Filed: Dec. 23, 2009

(65) Prior Publication Data

US 2010/0106090 A1   Apr. 29, 2010

Related U.S. Application Data

(63) Continuation-in-part of application No. PCT/EP2008/004951, filed on Jun. 19, 2008.

(30) Foreign Application Priority Data

Jul. 24, 2007 (DE) .......................... 10 2007 034 871

(51) Int. Cl.
*A61M 5/00* (2006.01)
*A61M 37/00* (2006.01)
*A61M 5/20* (2006.01)
*A61M 5/30* (2006.01)

(52) U.S. Cl. ........... 604/110; 604/131; 604/135; 604/68

(58) Field of Classification Search .................. 604/110, 604/131, 135, 68
See application file for complete search history.

(56) References Cited

U.S. PATENT DOCUMENTS

| | | | |
|---|---|---|---|
| 3,557,784 A | 1/1971 | Shields | |
| 4,185,628 A | 1/1980 | Kopfer | |
| 4,553,962 A * | 11/1985 | Brunet | 604/198 |
| 5,520,639 A * | 5/1996 | Peterson et al. | 604/68 |
| 5,681,291 A | 10/1997 | Galli | |
| 6,235,004 B1 * | 5/2001 | Steenfeldt-Jensen et al. | 604/207 |
| 6,258,068 B1 | 7/2001 | Kirchhofer et al. | |
| 2001/0051789 A1* | 12/2001 | Parsons | 604/68 |
| 2003/0105430 A1 | 6/2003 | Lavi et al. | |
| 2003/0139706 A1 | 7/2003 | Gray | |
| 2005/0273048 A1 | 12/2005 | Landau | |
| 2006/0178630 A1* | 8/2006 | Bostrom et al. | 604/135 |
| 2007/0049864 A1* | 3/2007 | Hansen | 604/68 |
| 2008/0140007 A1* | 6/2008 | Glynn | 604/135 |
| 2008/0262436 A1* | 10/2008 | Olson | 604/198 |

FOREIGN PATENT DOCUMENTS

| | | |
|---|---|---|
| DE | 1 798 824 | 10/1959 |
| DE | 101 02 054 A1 | 8/2002 |
| EP | 1 336 419 A1 | 8/2003 |

* cited by examiner

*Primary Examiner* — Nicholas Lucchesi
*Assistant Examiner* — Ian Holloway
(74) *Attorney, Agent, or Firm* — R. S. Lombard; K. Bach (57) ABSTRACT

A disposable injector with a housing (10) in which a mechanical spring energy reservoir, a cylinder/piston unit (100), a piston-actuating ram (60) and a trigger unit are arranged, wherein the spring energy reservoir comprises at least one pretensioned spring element, wherein at least part of the piston-actuating ram is positioned between the spring energy reservoir and the piston of the cylinder/piston unit, and wherein the piston (111) of the cylinder/piston unit is separately moveable via pump rod (140). The pump rod can be coupled releasably to the piston or to a piston rod of the piston. The cylinder of the cylinder/piston unit has a rear sealing element (105) that permits sterile closure of the cylinder interior located between the piston and the cylinder.

20 Claims, 6 Drawing Sheets

DISPOSABLE INJECTOR WITH MANUALLY ACTUATED PISTON

CROSS-REFERENCE TO RELATED APPLICATION

This is a continuation-in-part application of pending international application PCT/EP2008/004951 filed Jun. 19, 2008 and claiming the priority of German Application No. 10 2007 034 871.3 filed Jul. 24, 2007.

BACKGROUND OF THE INVENTION

The invention relates to a disposable injector with a housing, in which or on which—respectively at least in certain areas—at least one mechanical spring-energy storage, at least one cylinder-piston unit which can be filled at least occasionally with active ingredient, at least one piston-actuating plunger and at least one actuating unit are arranged, whereby the spring-energy storage includes at least one pre-stressed spring-loaded element, whereby at least part of the piston-actuating plunger is positioned between the spring-energy storage and the piston of the cylinder-piston unit and whereby the piston of the cylinder-piston unit—with a prestressed spring element—can be moved separately via a pump rod.

US 2001/0051789 A1 discloses inter alia such an injector which has a spring pre-stressed piston-actuating plunger which, upon actuation of the injector, acts on a rigid combination of piston and piston rod of the piston guided in the cylinder-piston unit. The one-piece piston rod is continued rearwards so far that its protrudes beyond the rear housing end of the injector. By means of the rear end of the piston rod, the piston can be moved separately by hand. The interior of the cylinder of the cylinder-piston unit cannot be closed off here in a sterile manner, and the entire piston rod is moved during the injection.

The present invention therefore addresses the problem of developing a modular disposable injector the cylinder-piston unit of which is able to be filled in the assembled state. This injector has only a few components for its minimal structural size and guarantees secure mounting and function with easy handling. The injection solution can be kept sterile for up to two years, even in the manually filled injector.

The object of the present invention is to provide a pump rod that can be coupled releasably to the piston or to a piston rod of the piston. The cylinder of the cylinder-piston unit has a rear sealing element that permits sterile closure of the cylinder interior located between the piston and the cylinder.

SUMMARY OF THE INVENTION

The present invention provides a disposable injector with a housing (10) in which a mechanical spring energy reservoir, a cylinder/piston unit (100), a piston-actuating ram (60) and a trigger unit are arranged, wherein the spring energy reservoir comprises at least one pretensioned spring element, wherein at least part of the piston-actuating ram is positioned between the spring energy reservoir and the piston of the cylinder/piston unit, and wherein the piston (111) of the cylinder/piston unit is separately moveable via pump rod (140). The pump rod can be coupled releasably to the piston or to a piston rod of the piston. The cylinder of the cylinder/piston unit has a rear sealing element (105) that permits sterile closure of the cylinder interior located between the piston and the cylinder.

The invention presents here for example a needle-free disposable injector, of which the cylinder-piston unit can be filled by a manual pump movement when the spring-energy storage is tensioned. For this purpose, a pump rod is coupled from outside into the piston of the cylinder-piston unit arranged in the injector, such that the piston can be moved by means of the pump rod. After correct filling, the cylinder-piston unit can be closed off again in a sterile manner using a sterile stopper. If appropriate, the pump rod is uncoupled and withdrawn from the housing. By a special arrangement of the sealing elements in the cylinder-piston unit, the filling remains closed off in a sterile manner.

BRIEF DESCRIPTION OF THE DRAWINGS

Further details of the invention will emerge from the following schematically illustrated embodiments, in which.

DETAILED DESCRIPTION OF THE PARTICULAR EMBODIMENTS

FIGS. 1 to 4 show a simplified main sketch of a disposable injector type with permanently loaded spring-energy storage in three different release states. The illustrated disposable injector comprises a housing (10), a cylinder-piston unit (100) pre-filled with e.g. an injection solution, a piston-actuating plunger (60) and a screw compression spring (50) as spring-energy storage. Also, an actuating element (82) and a retaining element (90) are arranged on the housing (10). The cylinder-piston unit (100) is sealed from the front by a sealing cap (120) in combination with a plug (128). The cylinder-piston unit (100) has a piston (111) which can be moved by means of a separate pump rod (140) in the cylinder (101).

The housing (10) is a pot-shaped hollow body, open at the bottom and with an elevated floor (39). The housing (10) has e.g. two opposite window-like openings (33) in the middle region, the shell region (31), as in FIG. 3. Articulated respectively at the lower edge of the single opening (33) is a compression bar (21). The floor (39) has a central bore (38).

The compression bars (21) are arranged here only by way of example in drag-hinges and supported by spring-loaded elements (52) on the housing (10). The spring-loaded elements (52) press the support rods (21) at least approximately radially outwards against the actuating element (82), as in FIGS. 1 to 4, where they rest on the actuating element (82) via cams (22). The cams (22) can also lie e.g. 5 to 20 millimeters beneath the respective free upper end of the compression bars (21). If the compression bars (21) are formed on the housing (10), as in FIGS. 5 to 8, they spring outwards as elastic flexional beams (28).

Figure 1:
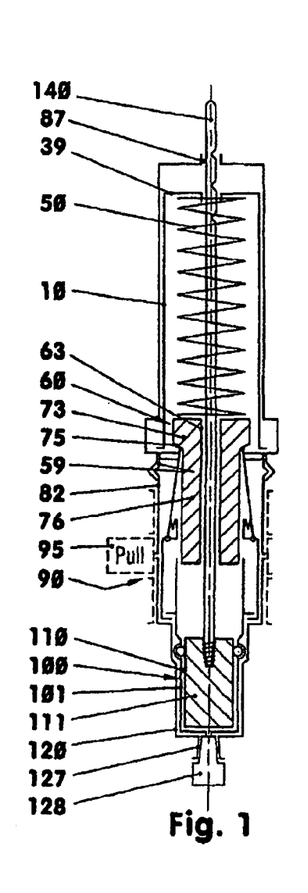
FIG. 1 illustrates a disposable injector with two compression bars and piston capable of pumping.
Figure 2:
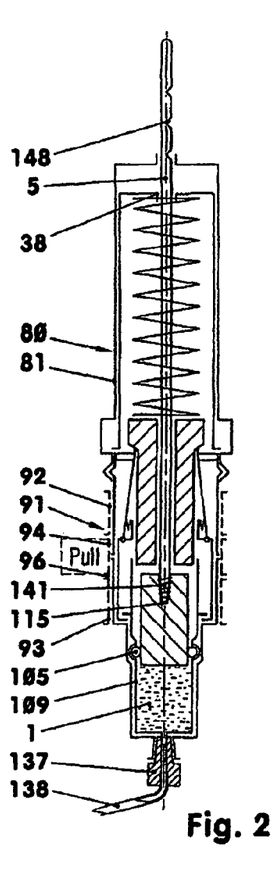
FIG. 2 as for FIG. 1, however with a manually filled cylinder.
Figure 3:
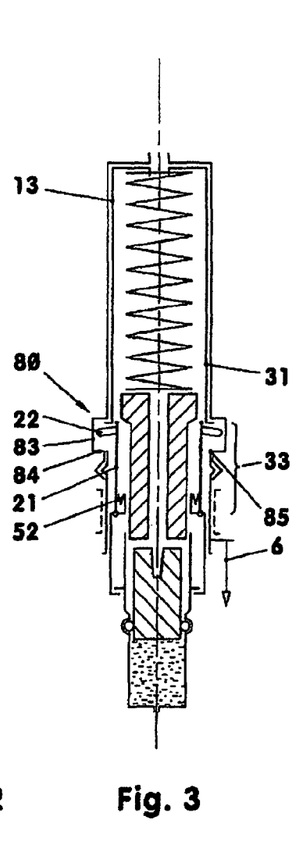
FIG. 3 as for FIG. 1, however unlocked and actuated and without a pump rod (fictitious state)
Figure 4:
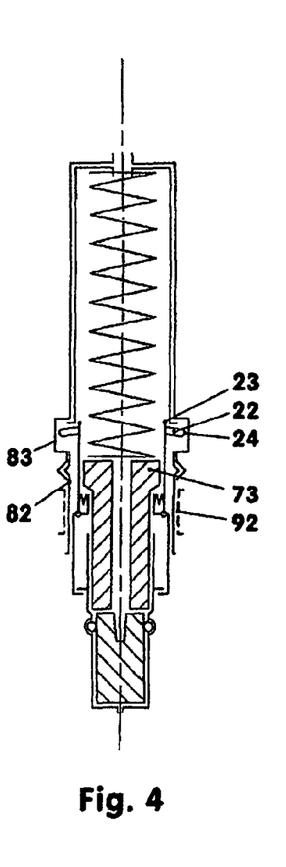
FIG. 4 as for FIG. 2, however following drug ejection.
Figure 5:
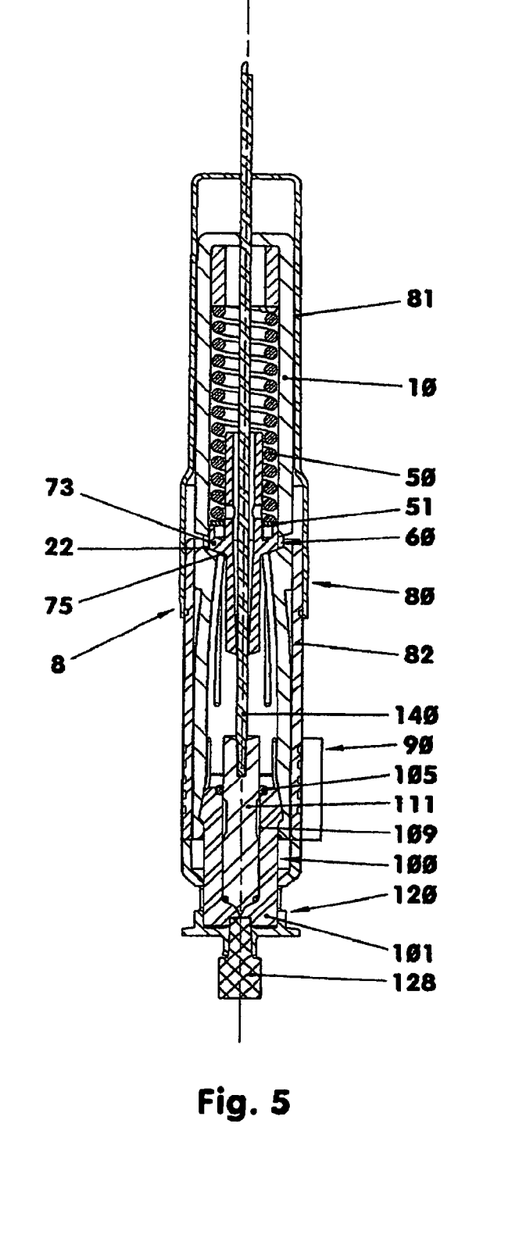
FIG. 5 illustrates a disposable injector with two compression bars deformed in locked position.

Both pressure-stressed compression bars (21) hold the piston-actuating plunger (60) on its plunger disc (73) in its pre-stressed position, as in FIG. 1. For this purpose, the compression bars (21) are supported on the plunger disc (73) by their support surfaces (23). The size of the respective contact surface between a support surface (23) and the corresponding site on the plunger disc (73) is in the region of 2 to 20 mm$^2$.

On the side averted from the centre line (5) each compression bar (21) has a contact surface (24) on its cam (22).

In the embodiment the cylinder-piston unit (100) comprises a transparent cylinder (101) filled with an injection solution (1), in which a piston (111) sits in the front position. The cylinder (101) has a cylinder inner wall (109) which, towards the rear, ends in an annular groove, for example. A sealing element (105), bearing tightly on the piston (111) in a radial direction, sits in the annular groove. The empty cylinder inner space (110), occupied for the most part only by the piston (111), is closed off in a sterile manner by the sealing element (105). Behind the annular groove, the cylinder (101) widens to such an extent that a rearwardly moved piston (111) cannot touch the wall of the widened area.

On its rear face, the piston (111) has a for example central, frustoconical recess (115) in which the pump rod (140) is screwed by means of a tapered thread (141). The pump rod (140) can be released from the piston (111) with minimal force.

Above the piston (111) in the housing (10) the piston-actuating plunger (60) is e.g. arranged such that although it does not touch the piston, it is guided sideways by its lower end, for example, in the upper region of the cylinder (101). The piston-actuating plunger (60) has a, for example central, bore (63), which is traversed by the pump rod (140).

According to FIG. 1 the lower half of the housing (10) is enclosed by the sleeve-like actuating element (82). The actuating element (82) is mounted to move lengthways on the radial outer surface (13) of the housing (10). It ends at the rear with a sharp edge (85). Below the edge (85), according to FIG. 1, the outer contact surfaces (24) of the cams (22) touch the inner wall (59) of the actuating element (82) in a securing manner.

For example, near the edge (85), an actuating cap (81) is secured on the actuating element (82) and completely surrounds the rear end of the housing (10). It has a central bore (87) there for passage of the pump rod (140). The actuating cap (81) comprises a peripheral widened region (83) in which the cams (22) are received when the injector is actuated. There can also be partially widened regions or uncovered openings instead of this widened region (83) in the case of a non-rotating symmetrical actuating element (82) per compression bar (21).

With respect to the housing (10) the widened region (83) is positioned and dimensioned so precisely that it can take up the outwards-thrust compression bars (21) with their cams (22) retreating during the triggering procedure. The inner contour of the widened region (83) is e.g. a channel with a return flank (84), which here represents a plane normal to the centre line (5) of the injector.

The piston-actuating plunger (60) arranged in the housing (10) is divided here into two regions. The lower region is the piston slide (76). Its diameter is somewhat smaller than the inner diameter of the rear region of the cylinder (101). The lower front end of the piston slide (76) acts directly on the piston (111).

The upper region of the piston-actuating plunger (60), that is the plunger disc (73), is a flat disc, cylindrical at least in certain areas, whereof the outer diameter is a few tenths of a millimeter smaller than the inner diameter of the housing (10) in the shell region (31). The lower front face (74) has a collar surface (75) arranged around the piston slide (76). It has the shape of a frustoconical surface, whereof the apex angle is ca. 100 to 130 degrees, preferably 120 degrees of angle. The notional tip of the frustoconical surface lies on the centre line (5) in the region of the piston slide (76). The collar surface (75) can also be spherically curved.

The piston slide (76) can of course also be designed as a separate component, separate from the plunger disc (73). For this purpose it is located on the inner walls of the housing (10).

The screw compression spring (50) sits pre-stressed between the plunger disc (73) and the superjacent floor (39) of the housing (10). The resilient force of the screw compression spring (50) is transferred via the plunger disc (73) to the compression bars (21). Due to the inclination of the collar surface (75) the compression bars (21) are thrust radially outwards in the manner of a bevel gear. The release sleeve (82) steadily supports this radial force.

Attached to the front end of the actuating element (82) is the sealing cap (120) which encloses the lower part of the cylinder-piston unit (100). The sealing cap (120) has an adapter opening (127) on the front end face with, for example, a Luer taper bore, which opening is sealed in a sterile manner by means of an externally tapered plug (128). Here the sealing cap (120) is mounted on the lower region of the housing (10). It and the sleeve-like actuating element (82) are encased at least in certain areas with an adhesive label (91). The adhesive label (91) comprises a main part (92), a tear-off banderole (94) and a cap part (93). The tear-off banderole (94) is connected to the label parts (92, 93) by a predetermined breaking point (96), e.g. a perforation or a continuous material thin-point. The tear-off banderole (94) is hereby arranged over the assembly joint laid between the actuating element (82) and the sealing cap (120) and ends in an upright tear-off tab (95).

An all-over adhesive label can also be used, which in the region of the assembly joint separating the parts (82) and (120) contains tearproof pull means. The pull means, e.g. a thread, a plastic strip, a thin wire or the like project to one side over the label. When the pull means are removed the label is specifically undone in the region of the assembly joint.

To be able to use the disposable injector, the cylinder-piston unit (100) must first be filled. For this purpose, the stopper (128) is removed from the adapter opening (127) and is replaced by a hose adapter (137). The latter has a pump hose (138). With the pump hose (138), the injection solution (1) is suctioned from an opened medicament ampoule into the cylinder (101), by the piston (111) being pulled back by means of the pump rod (140). The amount of injection solution (1) suctioned can be controlled via the scale (148) located on the pump rod (140). The suctioning operation is completed by the gas bubbles, which may have been sucked into the cylinder (101), being removed in a known manner, for example by sliding the piston (111) slightly back, with the sealing cap (120) held upwards. Two windows (126) arranged in the sealing cap (120) serve for control purposes (see FIG. 10). Then, for example, the pump rod (140) is turned out of the recess (115) of the piston (111) and withdrawn from the housing (10).

To activate the injector the tear-off banderole (94) is removed so that the adhesive connection between the sealing cap (120) and the actuating element (82) is broken. The sealing cap (120) and the hose adapter (137) are pulled off. The disposable injector is positioned on the injection site. The actuating element (82) can now be pushed in the direction of the cylinder-piston unit (100), as in FIG. 3. During this procedure the actuating element (82) slides on the outer walls (13) of the housing (10) downwards and linearly, therefore in the direction of the injection site. The contact surfaces (24) of the compression bars (21) skid over the edge (85) and spring radially outwards in release into the widened region (83) under the force of the spring-loaded element (50). The piston-actuating plunger (60) shoots unhindered downwards, as in FIG. 4. The cylinder (100) is emptied.

A helical movement can also be provided instead of a linear sliding motion of the actuating element (82) on the housing (10). In this case the actuating element (82) and the housing (10) are guided towards one another e.g. via a slide block and a motion link. If required, triggering can also be realized by a pure pivoting movement between the housing (10) and the actuating element (82). The pivot axis here would be the centre line (5).

FIGS. 5 to 10 show an embodiment of the principle described in FIGS. 1 to 4. Here the load-bearing component is a one-piece housing (10). It is made from e.g. a fiberglass-reinforced polyamide by injection molding. The housing (10) has an extensively tubular shape and is divided into two functional areas, comprising both the upper shell region (31) and the lower fixing region (41).

Figure 7:
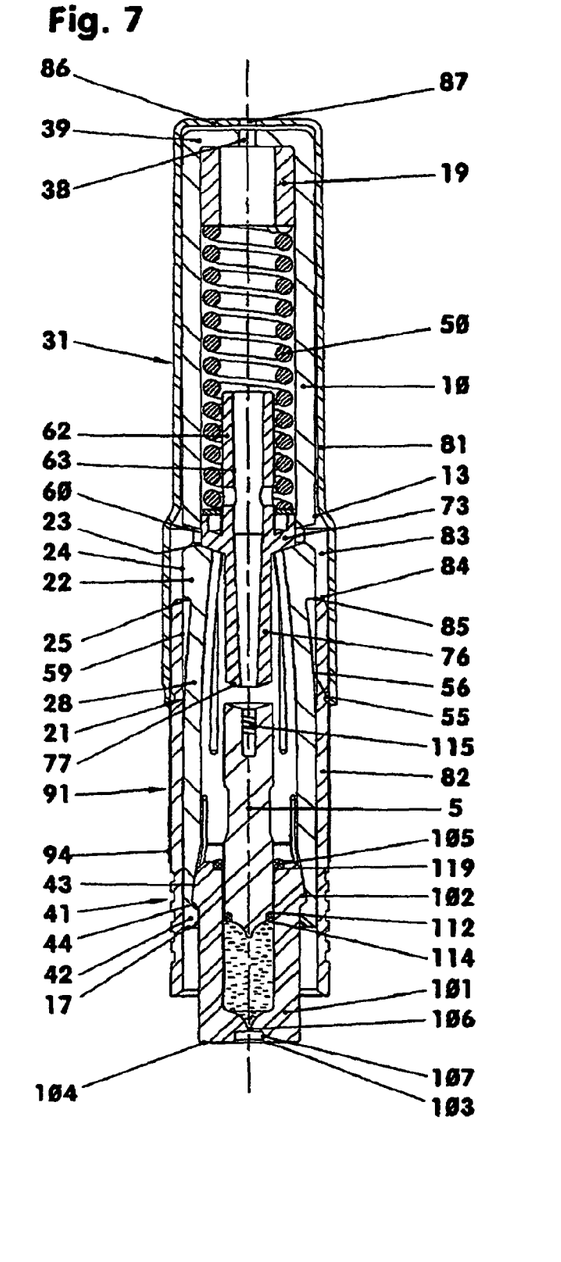
FIG. 7 as for FIG. 6, however unlocked and actuated (fictitious state)

The substantially tubular shell region (31) is sealed at the top by an e.g. level floor (39) with an integrated bore (38), as in FIG. 7. Located in the lower half of the shell region (31) are two opposite formed-on compression bars (21). The forming-on site for the compression bars (21) is just above the fixing region (41). For forming the respective compression bar (21) there is located in the lower region of the shell section (31) a narrow, at least approximately U-shaped gap, surrounding the individual compression bar to the sides and at the top. Over ca. 80% of its length the compression bar (21) has the wall thickness and curve of the walls of the housing (10). This region inter alia also functions as a sprung-elastic flexional beam (28) and has a sickle-shaped cross-section.

Figure 8:
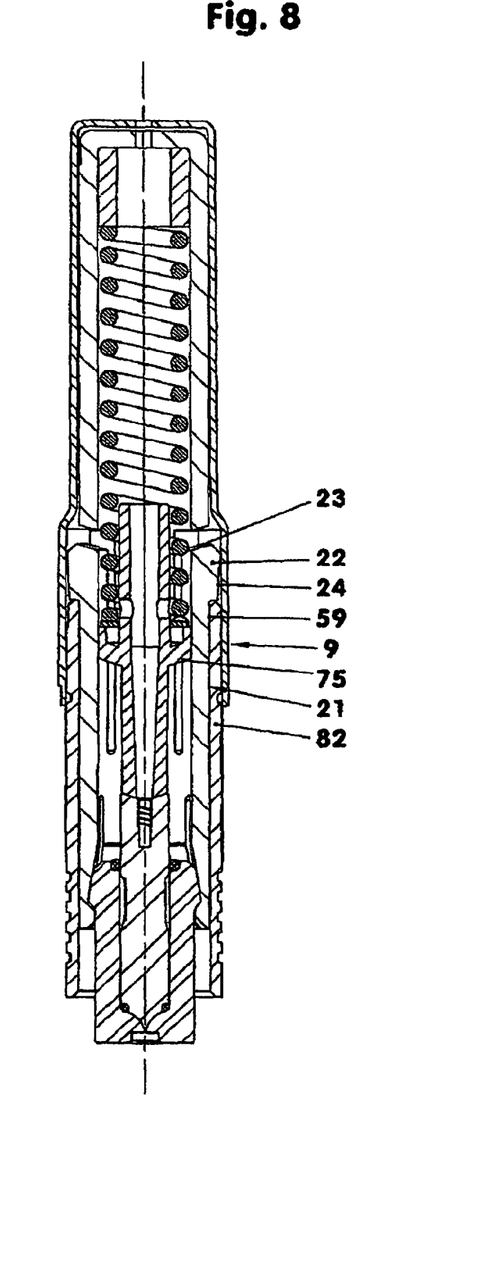
FIG. 8 as for FIG. 7, however with emptied cylinder.

If required, part of this flexional beam (28) can also be equipped with a rectangular cross-section to reduce bending stresses occurring from use in the flexional beam edge region. In FIG. 8 the compression bar (21) is shown in the undeformed state.

The upper free end of the individual compression bar (21) is here formed by the radially outwards projecting cam (22), which has at least one support surface (23) and one contact surface (24). According to FIG. 5 the plunger disc (73) of the stressed disposable injector lies on the support surface (23) by its collar surface (75). The support surface (23), here fulfilling the function of a wedged face, has the form of a frustoconical surface with an apex angle of 120 degree of angle.

At least in the contact region the compression bars (21) or the collar surface (75) may have ceramic armoring. If required, the collar surface (75) is reinforced by an e.g. stuck-on frustoconical surface-shaped washer.

The contact surface (24) of the cam (22), as in FIG. 8, is part of a cone, whereof the maximum diameter is e.g. 3 to 4 millimeters larger than the outer diameter of the housing (10). When the disposable injector is stressed the contact surface (24) contacts the inner walls (59) of the sleeve-like actuating element (82). If required, to minimize the surface pressure the contact surface (24) has a curve, which corresponds to the inner walls (59), as in FIGS. 5 and 6.

Figure 11:
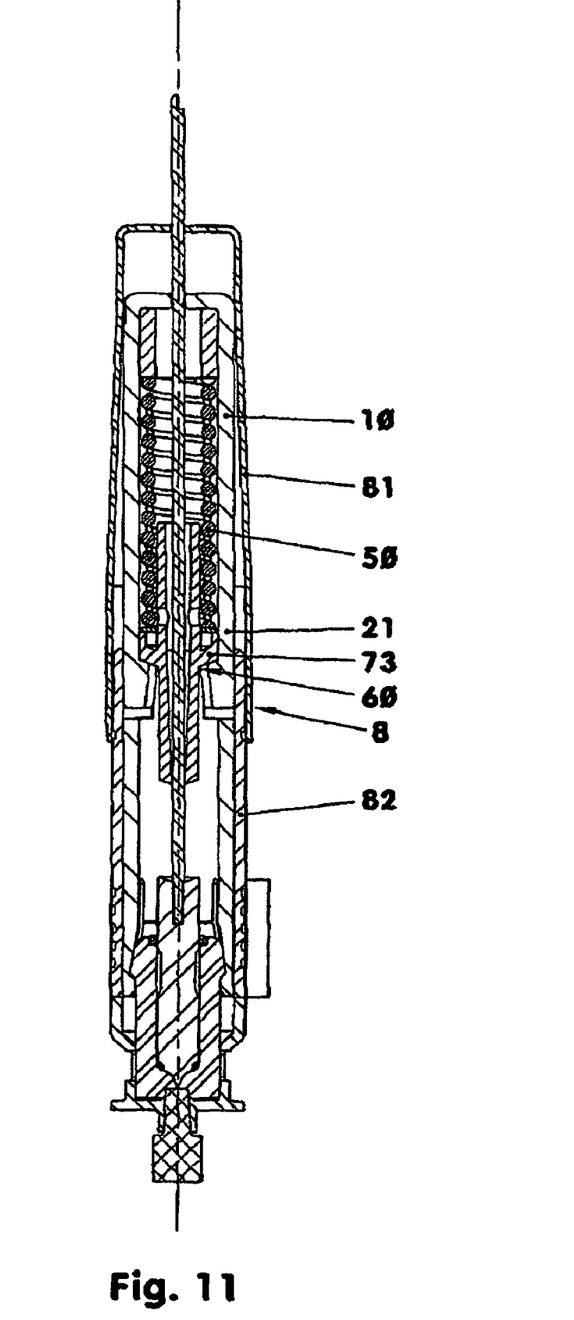
FIG. 11 illustrates a disposable injector in locked position with two draw hooks and piston capable of pumping.

As an alternative to the compression bars (21), it is also possible to use drawbars, as in FIG. 11. These drawbars (21) are formed integrally in the upper area of the housing. With the spring-energy storage (50) tensioned, they engage the plunger disc (73) of the piston-actuating plunger (60) from above. In order to give the outwardly pivoting drawbar (21) enough free space when the injector is operated, the actuating cap (82) in this variant is at least in some areas configured as a frustoconical shell.

Situated under the shell section (31) is the fixing region (41) for taking up the incorporable cylinder-piston unit (100), as in FIG. 7. The fixing region (41) includes e.g. eight spring hooks (42) aligned parallel to the centre line (5). The spring hooks (42) have respectively an at least double-flank rear grip for possibly snugly receiving the cylinder-piston unit (100). The opposing flanks (43, 44) of the rear grip (42) enclose, as in FIG. 7, an angle of e.g. 127 degrees of angle. The lower flank (44) has a cone angle of 45 degrees, with its cone tip lying on the centre line 5, as viewed in the direction of the nozzle (106), below the front end (17). The length and the resilient rate of the spring hooks (42) are such that the cylinder (101) can be incorporated without plastic deformation of the spring hooks (42).

Figure 9:
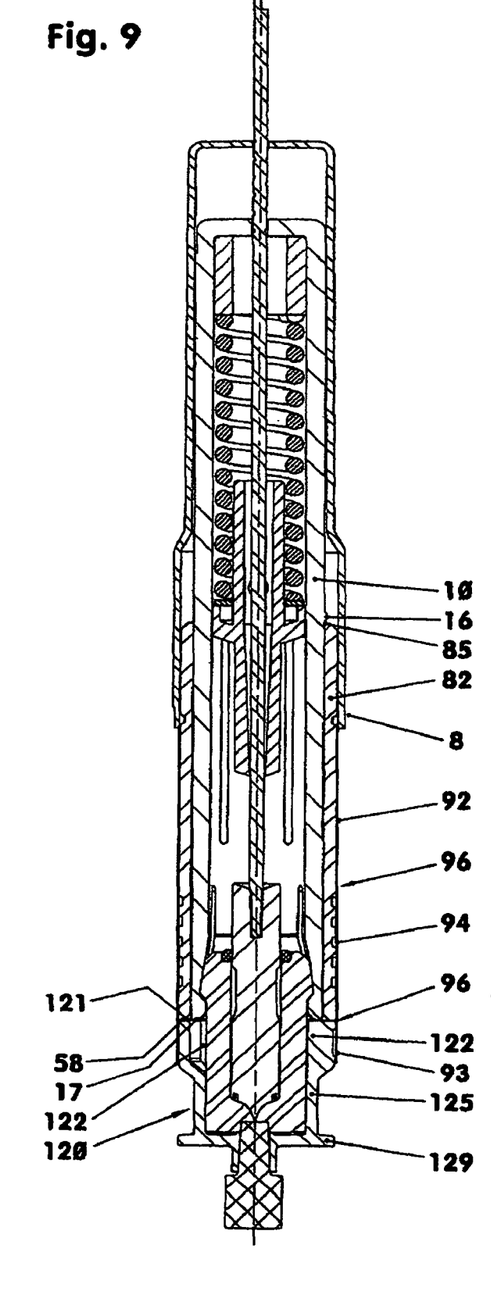
FIG. 9 as for FIG. 5, however rotated 90° about the injector centre line.

To be able to fix the housing (10) securely together with the spring-loaded element (50) and the piston-actuating plunger (60) in the actuating element (82) during installation, the housing (10) has, in an area between the cams (22), a lenticular elevation (16), cf. FIG. 9, via which the housing (10) bears on the edge (85) of the actuating element (82).

The cylinder (101) is e.g. a transparent, thick-walled pot, whereof the outer walls, cylindrical at least in parts, bear a, for example, circumferential latching rib (102) where required, which abuts the flanks (43, 44) of the rear grip of the spring hooks (42) dimensionally stably. In the area of the rear face of the cylinder (101), a collar (119) for receiving a sealing element (105) is situated on the upper end of the cylinder inner wall (109). If appropriate, the collar can also be a radial, annular turned groove that surrounds at least part of the sealing element with a form fit. Alternatively or in addition, the sealing element (105) can be adhesively bonded to the cylinder. The sealing element (105) is depicted as an O-ring in the illustrative embodiments. However, it can also be a quad ring, a lip seal or another equivalent sealing element.

Located in the centre of the bore of the cylinder (101), whereof the cylindrical floor matches the contour of the front piston front face at least approximately, is a short cylindrical, nozzle-like bore (106). Its diameter is ca. 0.1 to 0.5 millimeters. This bore (106) is one to five times as long as its diameter. It ends in a cylindrical or conical recess (107) of the floor-side outer front end (103) of the cylinder (101). The recess (107) constitutes at least approximately the front one to two millimeters of a Luer tapered bore. This front end (103) can be additionally fitted with an adhesive ring (104) to boost the application safety.

The cylinder (101) is, for example, made of the amorphous thermoplastic cycloolefin copolymer (COC). This material is virtually impermeable to water vapor, which permits long-term storage of the injection solution.

The rodless piston (111) sits in the for example cylindrical or conical bore of the cylinder (101). At its at least approximately conically configured front end face, the piston (111), which is made for example of the Teflon® derivative tetrafluoroethylene/hexafluoroethylene copolymer (FEP), has an axial annular groove (112) for receiving a sealing ring (114) or a permanently elastic sealing compound. Teflon is a registered U.S. Trademark of E.I. DuPont De Nemours and Company, 1007 Market Street, Wilmington, Del. 19898. The length of the piston (111) is chosen such that the inserted piston (111), cf. FIG. 5, 8 or 9, protrudes at least one millimeter beyond the rear top edge. The middle area of the piston (111) is narrowed. The narrowed area has a length corresponding to ca. 30% of the total length of the piston. The narrowed area has a diameter that is 16 to 20% smaller than the maximum inner diameter of the cylinder in the area of the cylinder inner space (110) receiving the solution. The front transition lying between the narrowed area and the front, i.e. in this case bottom, piston area has a cone angle of 35 to 40 degrees, for example. The other, rear transition has a cone angle of between 35 and 90 degrees.

Figure 12:
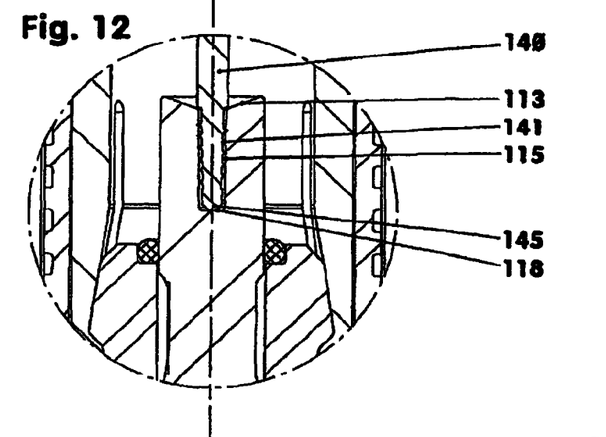
FIG. 12 is a detail enlargement of FIG. 5.

In the rear, for example frustoconical, end face (113) of the piston (111) there is a central, conical piston recess (115) with the floor (118), cf. FIG. 12, for coupling the pump rod (140). The cone angle of the piston recess (115) is, for example, one degree. At its lower end, according to FIG. 12 inter alia, the pump rod (140) has a conical V-thread (141) for coupling to the piston (111). The cone angle of the V-thread (141) is six degrees, for example. When the pump rod (140) is turned into the piston recess (115), the thread pitch of the V-thread (141) presses in the necessary counter-thread. The turning-in operation is completed when the front end of the pump rod (140) contacts the floor (118) with the narrow tip of the frustoconical end face (145).

Figures 13, 14:
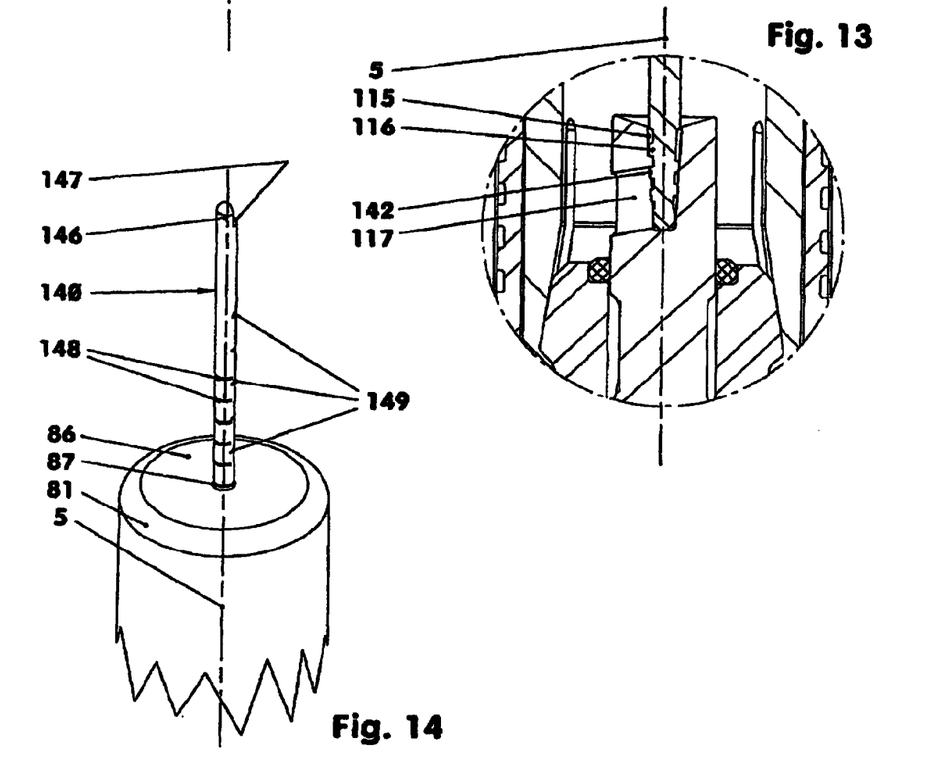
FIG. 13 is an alternative detail enlargement of FIG. 5.
FIG. 14 is a detail enlargement of FIG. 10.

FIG. 13 shows, as the coupling between the pump rod (140) and the piston (111), a conical trapezoid thread (142) that engages in a piston recess (115) in which at least one partial pitch (116) or a cam is arranged. The partial pitch (116) shown extends in cross section, i.e. perpendicular to the centre line (5), over 30 to 60 degrees. The axial forces to be transmitted from the pump rod (140) to the piston (111) are conveyed only via the partial pitch (116). For reasons of production engineering, an oblong hole (117) is located below the partial pitch.

Both separate threads (141, 142) used for coupling purposes require only minimal screwing-in and screwing-out forces. Other releasable couplings can of course also be used, for example, a key/keyhole system or a simple catch system.

The pump rod (140) has, for example, a constant cross section along most of its length. Its maximum diameter in the illustrative embodiment is ca. two millimeters. It is made, for example, of a polyamide reinforced with glass fibers. At its rear end, which protrudes from the bore (87) of the actuating cap (81), it has two differently graded scales (148) and (149), cf. FIG. 14 inter alia. The scale (148) is for a cylinder-piston unit (100) whose cylinder (101) has an average inner diameter of seven millimeters, while the other scale (149) is for a cylinder (101) with an inner diameter of six millimeters. The different-sized cylinders (101) can be inserted into the injector alternately.

Both scales (148, 149) each have horizontal division marks. These division marks lie in planes that are oriented perpendicular to the centre line (5). Each division mark has, for example, the length of half the circumference of the pump rod. The division marks of one scale (148, 149) all lie above one another. They can, for example, be colored, black or white division marks or can be formed as notches in the pump rod. Instead of the division marks, dots or numbers can also be used.

If appropriate, the rear end of the pump rod (140) can be provided with a structure, for example transverse or longitudinal grooves, a fluting or the like. The cross section can also be flattened in areas or can have a greater diameter than the area that extends through the piston-actuating plunger (60).

According to FIG. 9, inter alia, the front scale (148) assigned to the larger cylinder is lengthened by half a cylinder (146) to make the allocation clear. The two lower division marks located directly on the level of the floor (86) mark the nominal volume of the respective cylinder (101). The in each case upper division mark indicates that the piston (111) is pushed completely into the cylinder (101). Each of the other division marks of the scales (148, 149) represents 0.1 milliliter, for example.

The spring-energy storage (50) or drive unit of the disposable injector is arranged between the piston (111) and the floor (39).

The spring-energy storage (50) is a screw compression spring, arranged on the piston-actuating plunger (60) with the plunger disc (73). It is supported on the upper floor (39) of the housing (10) with interpositioning of a spacer sleeve (19). The resilience-stressed piston-actuating plunger (60) is supported on the compression bars (21) of the housing (10) by means of the plunger disc (73).

Above the plunger disc (73) the piston-actuating plunger (60) has a pilot pin (62) which guides the screw compression spring (50) or is guided thereby. Located centrally under the plunger disc (73) in the extension of the pilot pin (62) is the piston slide (76), which acts on the piston (111) when the disposable injector is actuated. The piston slide (76) has a frustoconical, forwardly curved front end (77), see FIG. 7 inter alia. With this front end (77), it contacts the matchingly shaped end face of the piston (111). Both cones have at least approximately the same cone angle.

In the embodiment the piston slide (76) ends e.g. 2 to 4 millimeters above the piston (111). The piston-actuating plunger (60) has a through-bore (63) whose upper half is substantially cylindrical, while its lower half narrows conically toward the bottom. In the area of the lower front end (77), the bore is only one to two tenths of a millimeter larger than the external diameter of the piston rod.

FIGS. 5 and 7 to 10 show a compression bar injector with an actuating unit (80) that almost completely encloses the housing. The actuating element (82), as part of the actuating unit (80), is also an actuating sleeve here. The substantially cylindrical actuating sleeve (82), made of acrylonitrile butadiene styrene (ABS) for example, has as its front end the return flank (84) with the inwardly lying edge (85). An actuating cap (81), which surrounds the rear end of the housing (10), is secured on the actuating element (82). The actuating cap (81) is for this purpose pushed over the rear end of the actuating element (82).

Figure 6:
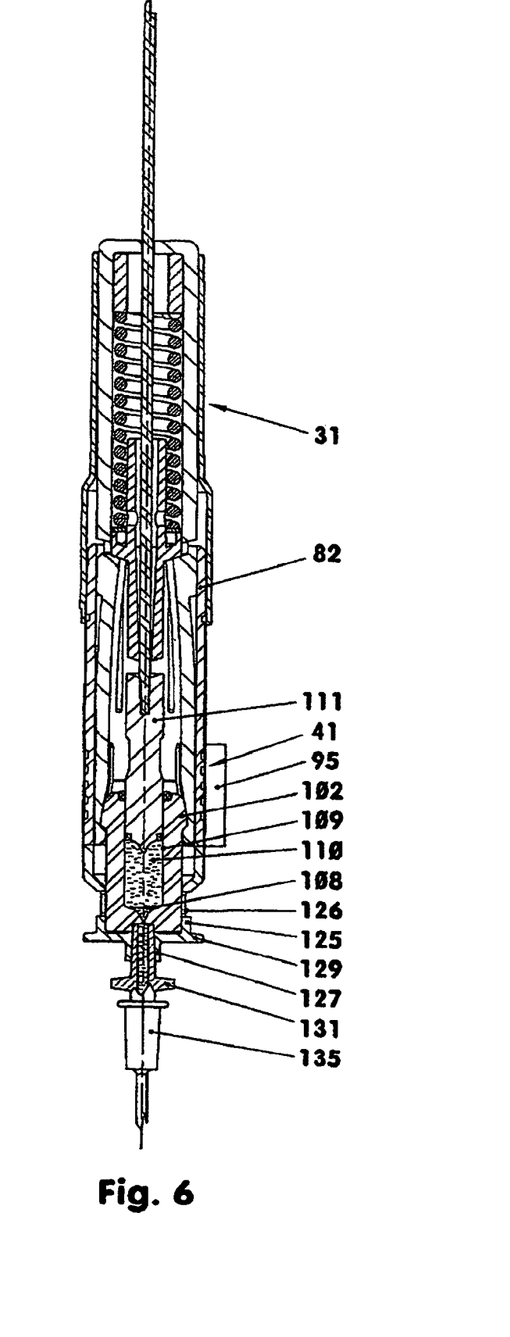
FIG. 6 as for FIG. 5, however loaded by means of an injection needle.

In FIG. 6, the rear end of the actuating cap (81) has been omitted only for illustration. The rear edge of the actuating cap (81), open at the rear, lies level with or below the housing floor (39) when the injector is not actuated, i.e. when it is in the locked position (8).

Directly above the return flank (84), the widened region (83) is located in the actuating cap (81). Above the widened region (83), the actuating cap (81) bears slidably on the outer wall (13) of the housing (10).

To secure the actuating cap (81) on the actuating element (82), the actuating element (82) has, for example, an annular groove (56) into which a peripheral web or detent cam (55) of the actuating cap (81) engages. If appropriate, in order to facilitate assembly, part of the actuating cap (81) has e.g. two lengthwise slits.

Figure 10:
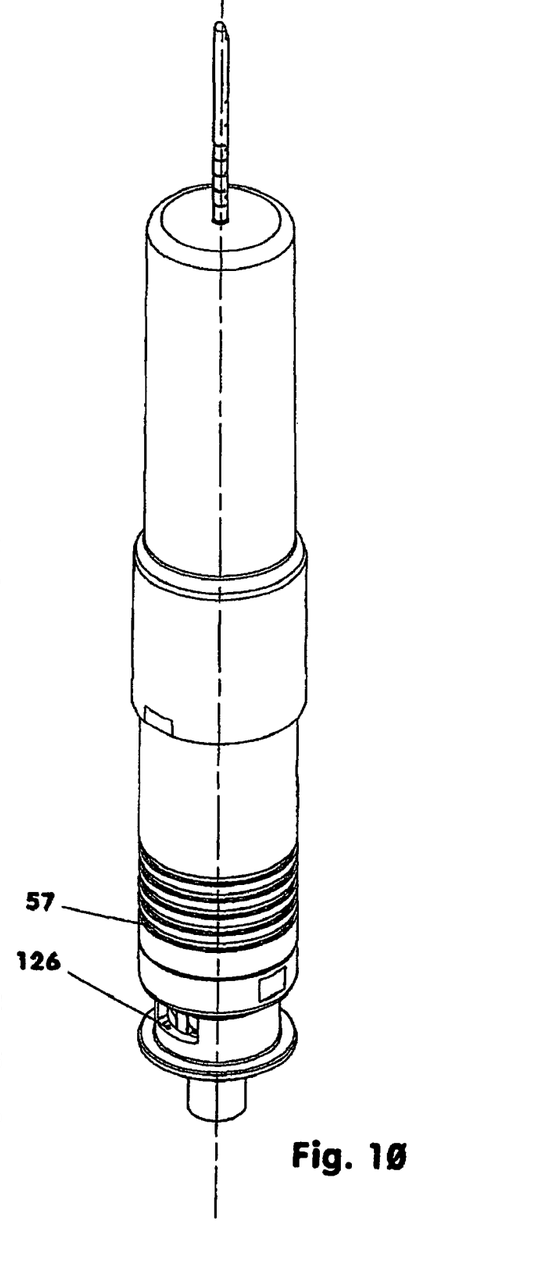
FIG. 10 is a diametrical view of FIG. 9, however without a label.

Located in the lower region of the actuating element (82) in its outer walls are several circumferential grooves (57), as in FIG. 10, or another comparable structure. The grooves (57) are e.g. equidistant from one another and extend over 10 to 30 millimeters of the length of the actuating element (82).

A centered sealing cap (120) rests on the lower front end (58) of the actuating element (82) on the cylinder (101) of the cylinder-piston unit (100). The at least approximately cylindrical outer surface of the sealing cap has the same diameter as the likewise cylindrical outer surface of the actuating element (82) in the vicinity of the front face (58).

The sealing cap (120) is a beaker which in a tightly fitting manner encloses at least the lower quarter of the cylinder-piston unit (100). With its pot area (125) part of the sealing cap (120) lies on the cylindrical outer walls of the cylinder (101) and on the lower front end (103) with the adhesive ring (104) attached there.

The sealing cap (120) in FIGS. 5, 6, 9 to 11 not only encases the cylinder (101) in certain areas and at the same time rests on the actuating element (82), but also is supported on the lower front end (17) of the housing (10) as in FIG. 9. For this purpose it has in the vicinity of the upper front end (121) several, for example five, contact links (122) arranged on the inner walls, aligned parallel to the centre line (5). The contact links (122) contact the outer wall of the cylinder (101).

The pot area (125) has two opposing windows (126), as in FIG. 6. The windows (126) have a width which corresponds to at least the diameter of the piston (111). The lower edge of the windows (126)—therefore the edges closest to the washer-like foot (128)—are arranged at the level of the cylindrical floor (108). The density of the cylinder filling can be checked using the windows (126) in the transmitted light inter alia. A frustoconical tube piece, for example, is formed integrally as adapter opening (127) on the washer-like foot (129). The adapter opening (127) has, as inner wall, at least in part a Luer taper bore. According to FIGS. 5, 9 and 10, the adapter opening (127) is closed off in a sterile manner.

The cylindrical actuating element (82) is sheathed over its entire length by an adhesive label (91). The adhesive label (91) itself is e.g. a paper and/or film strip coated on one side by an adhesive in certain areas. In one layer the film strip once surrounds e.g. the compound of sealing cap (120) and actuating element (82). As an original fastener (90) it comprises three separate strips which can be detached towards one another respectively by a perforation (96). The upper strip is the main part (92), the middle strip is a tear-off banderole (94) with a two- to three-centimeter-long tear-off tab (95) and the lower strip is the cap part (93). The main part (92) and the cap part (93) carry an adhesive layer, to which they are attached on the actuating element (82).

According to FIG. 6, an injection needle (135) is used to fill the cylinder (101). It sits via a double-cone adapter (131) in the adapter opening (127). The latter, together with the recess (107), forms at least approximately a Luer taper bore. For filling purposes, the piston (111) is pulled back with a suction action by means of the pump rod (140). The rear sealing element (105) remains fixed in position on the collar (119), even when the narrowed area of the piston (111) passes the sealing element (105). When the piston (111) has reached its rear position, cf. FIG. 6, the sealing element (105) again bears radially on the piston (111) in a sterile and leak tight manner. The combination of the sealing elements (114) and (105) ensures a sterile cylinder inner space (110) even during the pump movement of the piston (111).

After the cylinder (101) has been filled and, if appropriate, had air removed from it, the adapter opening (127) together with the recess (107) can be closed off again at the front in a sterile manner by means of a sterile stopper (128), in order to permit interim storage of the filled injector.

To activate the disposable injector the tear-off banderole (94) is separated all around from the main part (92) and from the cap part (93) by means of the tear-off tab (95). The grooves (57) of the actuating element (82) become visible. The sealing cap (120) is now peeled off downwards from the cylinder (101), as in FIG. 7. The injector is now set onto the injection site and the sleeve-like actuating element (82) pushed downwards in the direction of the injection site. The compression bars (21) bend elastically outwards into their actual starting position. At this point, the cams (22) slip over the edge (85) outwards into the widened region (83). The compression bars (21), no longer deformed, release the piston-actuating plunger (60), so that the piston (111) is suddenly moved downwards to empty the cylinder (101), as in FIG. 8. During the forward movement of the piston (111), the piston friction decreases in the meantime, since the rear sealing element (105) does not bear with a braking action as it passes the narrowed piston area.

Should the injector not actuate, the injection solution can also be applied by means of an injection needle (135). For this purpose, the injection needle (135) is clamped in the recess (107) with the aid of a double-cone adapter (131). With a pump rod (140) screwed into the recess (115) of the piston (111), cf. FIG. 6, the injector can be used like a conventional disposable syringe.

In this variant embodiment, with the exception of the spring-loaded element (50), all components can be arranged rotationally symmetrically and/or mirror-symmetrically to a plane laid on the centre line (5).

With injectors, in which the piston-actuating plunger (60) is guided straightly in the housing (10)—at least in certain areas—with minimal clearance and the piston-actuating plunger (60) has adequate bending strength, only a single compression bar (21) can be used instead of two or more compression bars (21).

In the variants illustrated in the figures the individual contact zone between the compression bar (21) and the plunger disc (73) is designed as surfaces (23) and (75), which glide on each other on contact. In a particular configuration in each surface (23) of the individual compression bars (21) a roller can be mounted, which rolls away as a roller bearing, therefore almost frictionless, when the injector is actuated on the surface (75) of the plunger disc.

With the exception of the spring-loaded element (50, 52), where required a piston plate and for example the available bearing roller of the support bars (21), all parts of the previously described disposable injectors are made of plastics or plastic- or rubber-like materials.

LIST OF REFERENCE SYMBOLS 1 injection solution; drug
5 centre line of the injector, lengthways direction
6 actuation direction of movement of (82), downwards movement directional arrow
8 locked position
9 actuating position, triggering position
10 housing, one-piece
13 outer surface, cylindrical
16 elevation, lenticular
17 front end, front, lower
19 spacer sleeve
21 compression bars, support rods; drawbar
22 cams
23 support surface
24 contact surface
25 rear grip flank
28 flexional beams
31 shell region
33 openings
38 bore
39 floor
41 fixing region for the cylinder-piston unit
42 spring hooks 43 flank, upper
44 flank, lower
50 spring-loaded element, screw compression spring, spring-energy
51 washer, planar
52 spring-loaded elements on (21)
55 detent cam
56 annular groove of (82)
57 grooves of (82)
58 front end of (82)
59 inner walls of (82)
60 piston-actuating plunger
62 pilot pin
63 bore, through bore
73 plunger disc
75 collar surface, conical
76 piston slide
77 piston slide front end, conical
80 actuating unit
81 actuating cap
82 actuating element
83 widened region
84 return flank
85 edge, sharp-edge
86 cap floor
87 bore
90 original fastener, banderole, retaining element
91 adhesive label
92 main part of (91)
93 cap part of (91)
94 tear-off banderole
95 tear-off tab
96 perforations, predetermined breaking points
100 cylinder-piston unit
101 cylinder
102 latching rib
103 front end
104 adhesive ring
105 sealing element
106 bore, nozzle
107 recess in the front end
108 cylindrical floor
109 cylindrical inner wall
110 cylinder inner space
111 piston
112 annular groove
113 front end, rear; cone
114 sealing ring, seal, sealing element
119 collar on (101)
120 sealing cap, adhesive seal
121 front end, top
122 contact links
125 pot area
126 windows, both sides
127 adapter opening
128 plug
129 foot, flange-like
131 double-cone adapter
135 injection needle
137 hose adapter
138 pump hose
140 pump rod
141 tapered thread, V-thread
142 special thread, tapered thread
145 end face, frustoconical
146 half cylinder
147 should (for small cylinder)
148 markings, half notches for large cylinders
149 markings, half notches for small cylinders

What is claimed is:

1. A disposable injector comprising:
a housing (10) having respectively at least in certain areas;
a mechanical spring-energy storage (50), a cylinder-piston unit (100) including a cylinder (101) having an inner wall (109) and an interior (110) which can be filled at least occasionally with active ingredient, a piston-actuating plunger (60) and an actuating unit (80) arranged for causing injection of the active ingredient;
the spring-energy storage (50) includes at least one pre-stressed spring-loaded element;
at least part of the piston-actuating plunger (60) is positioned between the spring-energy storage (50) and a cylindrical piston (111) of the cylinder-piston unit (100), the cylindrical piston (111) occupying substantially all of the interior (110) of the cylinder (101) when the cylinder is empty, the cylindrical piston (111) having a narrowed middle area between a front widened end and a rear widened end of the cylindrical piston (111), the front and rear widened ends of the cylindrical piston (111) each having a diameter approximating the diameter of the inner wall (109) and each widened end in slideable contacting relationship with the inner wall (109), the narrowed middle area of the cylindrical piston (111) having a predetermined length and in non-contacting relationship with the inner wall (109);
a pump rod (140) coupled releasably to the piston (111) or to a piston rod of the piston (111), the piston (111) of the cylinder-piston unit (100)—with a pre-stressed spring element—separately moveable via the pump rod (140);
the piston-actuating plunger (60) has a central bore (63) through which the pump rod (140) extends; and,
the inner wall (109) of the cylinder (101) has a first annular groove (119) therein proximate the rear thereof, a rear sealing element (105) operatively mounted in the first annular groove (119) and affixed to the inner wall (109) in sterile sealing relationship with and bearing radially against the rear widened end of the cylindrical piston (111) when the cylindrical piston is in radial alignment with the rear sealing element (105), and the rear sealing element 105 in sterile sealing relationship with and bearing radially against the front widened end of the cylindrical piston (111) when in radial alignment with the front widened end and, the rear sealing element (105) in non-contacting relationship with the narrowed middle area of the cylindrical piston (111) when in radial alignment with the narrowed middle area of the cylindrical piston (111), the seal (105) immediately after activation of the actuation unit (80) for imparting an initial braking action to the cylindrical piston (111) until the seal (105) is in radial alignment with the narrowed middle area of the cylindrical piston (111) where the initial braking action is released the pump rod (140) separated in sealed-off relationship from the interior (110) of the cylinder (101) by the cylindrical piston (111) and the sealing element (105.

2. The disposable injector according to claim 1, wherein the pump rod (140), at its rear end, protrudes from the housing (10), the pump rod (140) further includes one or more scales (148, 149) delineated thereon.

3. The disposable injector according to claim 2, wherein the scales (148,149) comprise several division marks or division-mark-like markings, where one division mark corresponds to the nominal volume of the cylinder (101), one division mark is a zero mark, and the other division marks represent subquantities of the nominal volume.

4. The disposable injector according to claim 2, wherein the rear end of the pump rod has two scales (148, 149), where the first scale (148) is provided for a cylinder (101) with a large cross section, and the second scale (149) is provided for a cylinder (101) with a small cross section.

5. The disposable injector according to claim 4, wherein the division marks of an individual scale (148, 149) are each semicircular marks or notches arranged above one another, the side of the pump rod (140) with the first scale (148) is lengthened by half a cylinder (146).

6. The disposable injector according to claim 1, further comprising the cylindrical piston (111) having a front end face having a second annular groove (112) therein proximate the front widened end of the cylindrical piston (111), a second sealing element (114) operatively mounted in the second annular groove (112) in sterile sealing relationship between the piston (111) and the cylinder (101).

7. The disposable injector according to claim 1, wherein the housing (10) includes at least one compression hook or draw hook (21), the at least one compression hook or draw hook (21) has at least one support surface (23) respectively in the region of its free end, on which the piston-actuating plunger (60) rests in a locking position of the at least one compression hook or draw hook (21), the actuating unit (80) further includes an actuating element (82), the at least one compression hook or draw hook (21) is secured in the locking position by the actuating element (82) positioned in a locked position (8), a sealing cap (120) is attached to the front end of the actuating element (82) for enclosing the lower part of the cylinder-piston unit (100), the actuating element (82) in the locked position (8) rests securely on the sealing cap (120), and the actuating element (82) has a triggering position (9) for effecting lateral retreat of the at least one compression hook or draw hook (21) when the piston-actuating plunger (60) is released.

8. The disposable injector according to claim 7, wherein the piston-actuating plunger (60) has on its front end averted from the spring-loaded element (50) at least in certain areas flat wedged faces or in certain areas single frustoconical faces (74, 75).

9. The disposable injector according to claim 7, wherein together with every single compression hook or draw hook (21) the piston-actuating plunger (60) forms a spline gear, in which an axial resilient force direction is deflected in a radial support force direction.

10. The disposable injector according to claim 7, wherein the single compression hook or draw hook (21) is formed respectively on the housing (10) and represents an elastic flexional beam (28).

11. The disposable injector according to claim 7, wherein the sealing cap (120) has an adapter opening (127) through the front end face thereof, the disposable injector further including an externally tapered plug (128) in removably engageable relationship with the sealing cap (120) proximate the adapter opening (127), whereby the cylinder (101) may be sealed in a sterile manner.

12. The disposable injector according to claim 11, further comprising a hose adapter (137) in removably engageable relationship with the sealing cap (120) proximate the adapter opening (127), the hose adapter (137) includes a pump hose (138), whereby an injection solution (1) may be suctioned from an opened medicament ampoule.

13. The disposable injector according to claim 11, further comprising a double-cone adapter (131) in removably engageable relationship with the sealing cap (120) proximate the adapter opening (127), an injection needle (135) in removably engageable relationship with the double-cone adapter (131), whereby an injection solution (1) from the injection needle (135) may be used to fill the cylinder (101).

14. The disposable injector according to claim 11, wherein the cylinder (101) includes a nozzle-like bore (106), the cylinder (101) proximate the bore (106) has a cylindrical or conical recess (107) at the floor-side outer front end (103) of the cylinder (101), a double-cone adapter (131) in removably engageable relationship with the recess (107) of the cylinder (101), an injection needle (135) in removably engageable relationship with double-cone adapter (131), whereby the pump rod (140) may be coupled to the piston (111) to actuate the injection needle (135) to provide for use of the injector as a conventional disposable syringe.

15. The disposable injector according to claim 7, wherein the cylinder (101) is transparent, the sealing cap (120) has a pot area (125), the pot area (125) has two opposing windows (126), whereby the density of the cylinder (101) filling can be visibly checked.

16. The disposable injector according to claim 1, wherein the rear end face (113) of the piston (111) has a central piston recess (115) with a floor (118), the lower end of the pump rod (140) has a conical V-thread (141) for coupling to the piston (111) proximate the piston recess (115), the piston recess (115) having counter-thread, whereby the pump rod (140) for engagement with the piston (111) is turned into the piston recess (115) until the front end of the pump rod (140) contacts the floor (118).

17. The disposable injector according to claim 1, wherein the rear end face (113) of the piston (111) has a central piston recess (115), the lower end of the pump rod (140) has a conical trapezoid thread (142) for engaging the piston recess (115), the piston recess has at least one partial pitch (116) or a cam arranged therein.

18. The disposable injector according to claim 1, wherein the pump rod (140) is made of a polymide containing glass fibers.

19. The disposable injector according to claim 7, further comprising an actuating cap (81) affixed to the actuating element (82), the actuating cap (81) in surrounding relationship with the rear end of the housing (10), the actuating cap (81) having a central bore (87), the pump rod (140) passes through central bore (87), the at least one compression hook or draw hook (21) includes cams (22) proximate the free end or ends thereof, the actuating cap (81) comprises a peripheral widened region (83) in operative receiving relationship with the cams (22) upon actuation of the injector.

20. The disposable injector according to claim 1, wherein the narrowed area of the cylindrical piston (111) has a length of about 30 % of the total length of the cylindrical piston (111).

* * * * *